(12) United States Patent
Suddath

(10) Patent No.: US 7,238,289 B2
(45) Date of Patent: Jul. 3, 2007

(54) FLUID TREATMENT APPARATUS

(75) Inventor: Ralph Suddath, Mason, TX (US)

(73) Assignee: Hydro Municipal Technologies, Ltd., Doss, TX (US)

( * ) Notice: Subject to any disclaimer, the term of this patent is extended or adjusted under 35 U.S.C. 154(b) by 0 days.

(21) Appl. No.: 10/479,123

(22) PCT Filed: May 30, 2002

(86) PCT No.: PCT/US02/16981

§ 371 (c)(1),
(2), (4) Date: Aug. 2, 2004

(87) PCT Pub. No.: WO02/096810

PCT Pub. Date: Dec. 5, 2002

(65) Prior Publication Data

US 2004/0251211 A1     Dec. 16, 2004

(51) Int. Cl.
   *C02F 1/30*     (2006.01)
   *C02F 1/32*     (2006.01)
   *C02F 1/48*     (2006.01)
   *B01J 19/12*    (2006.01)

(52) U.S. Cl. ........... 210/748; 210/198.1; 210/512.1; 422/186; 422/186.29; 422/186.3

(58) Field of Classification Search .......... 210/748, 210/198.1, 512.1; 422/186, 186.29, 186.3
   See application file for complete search history.

(56) References Cited

U.S. PATENT DOCUMENTS

| | | | | |
|---|---|---|---|---|
| 4,008,045 A | * | 2/1977 | Free | 250/436 |
| 4,141,686 A | * | 2/1979 | Lewis | 250/436 |
| 5,068,030 A | * | 11/1991 | Chen | 210/95 |
| 5,085,783 A | | 2/1992 | Feke | |
| 5,224,604 A | * | 7/1993 | Duczmal et al. | 209/12.2 |
| 5,300,019 A | | 4/1994 | Bischof et al. | |
| 5,393,421 A | * | 2/1995 | Ohe et al. | 210/223 |
| 5,439,595 A | * | 8/1995 | Downey, Jr. | 210/748 |
| 5,616,250 A | | 4/1997 | Johnson et al. | |
| 5,711,950 A | | 1/1998 | Lorenzen | |
| 5,779,912 A | * | 7/1998 | Gonzalez-Martin et al. | 210/748 |
| 5,925,246 A | | 7/1999 | Lee et al. | |
| 6,180,014 B1 | | 1/2001 | Salama | |
| 6,193,878 B1 | * | 2/2001 | Morse et al. | 210/85 |
| 2001/0042802 A1 | | 11/2001 | Youds | |

FOREIGN PATENT DOCUMENTS

| | | |
|---|---|---|
| DE | 39 08 704 | 9/1990 |
| DE | 38 40 364 | 12/1990 |
| EP | 0 083 444 | 7/1983 |
| EP | 0 290 609 | 11/1988 |
| RU | 2 135 041 | 8/1999 |
| WO | 98/24727 | * 6/1998 |

* cited by examiner

*Primary Examiner*—Thomas M. Lithgow
(74) *Attorney, Agent, or Firm*—Mark H. Miller; Jackson Walker LLP

(57) ABSTRACT

An apparatus that introduces rapidly spinning vortices in a fluid with a vortex cration device (2) and a frequency generation device (26).

7 Claims, 10 Drawing Sheets

FLUID TREATMENT APPARATUS

BACKGROUND OF THE INVENTION

1. Field of the Invention

Applicants' invention relates to a device for treating fluids and a method for same. More specifically, it relates to a fluid, and particularly water, treatment system to reduce bacteria, algae, and fungus in the fluid without the use of chemicals.

2. Background Information

Earth's water is continually cycled via a natural circulation system. Water moves from pools, streams, lakes, and rivers to the sea, it evaporates and enters the atmosphere, falls from the air back to earth, is absorbed into the ground, collects in underground aquifers, and re-emerges from underground through springs.

Water that has not been substantially affected by humans may be referred to as "natural water." Humans use the circulating "natural" water and then returning it to the circulation cycle. Unfortunately, often humans' use pollutes the water, resulting in "unnatural water." "Unnatural water" attracts and is susceptible to the growth of unhealthy bacteria, algae, and fungus. It has an altered state of pH, and a higher surface tension than "natural water."

Water emits an electromagnetic frequency (EMF) that can be measured. Natural water has its own EMF signature. However, water is an energy seeking substance that picks up frequencies from minerals, chemicals, and other substances it contacts. When this happens the water's EMF signature is altered to mimic that of the impurities. Thus, water can be said to have "memory." Even though water can be chemically or mechanically "purified" with the intention of ridding the water of as many poisonous substances as possible, it still carries memorized electrical frequencies, in specific frequency bands (wavelengths). After any purification, chemical treatment, filtration, or even after distillation, the pollutants' harmful information remains in the water. The memorized EMF signature can be tracked precisely to the detrimental substances which were in the water before treatment.

As noted in U.S. Pat. No. 5,711,950, "when sodium chloride is dissolved in water, water molecules surround the sodium and chloride ions to produce ion hydrates. The resulting geometry or the water molecules differs from, that of the prior clusters of hydrogen-bonded water molecules. The water molecules become more highly ordered and regular in structure. The addition of sodium chloride to microclustered water effects the same result. Thus, the sodium chloride may be said to function as a "template" for the change. This template or "pattern" is what secures the change in the water, locking in the extraordinary structure produced by this invention."

A molecule's shape can be as important to function as its composition. Electronic bonding patterns, determined by cluster shape, alter the behavior and properties of all phases of matter. When electrons are shared by the whole cluster in a de-localized pattern, negative charge is evenly distributed and the cluster may take on certain aspects of solid metal, such as conductivity. When the electrons are all tightly bound to atoms, the clusters resemble discrete molecules.

The covalent bonding of two hydrogen atoms to one oxygen atom forms the water molecule ($H_2O$). To complete its outer shell, oxygen needs two electrons, and it obtains these by sharing an electron with each or two hydrogen atoms. These bond to the oxygen atom to form a triangular structure. This shape is important because if forms the basis for many of the solutions and compounds that support life.

A water molecule's covalent bonds are polar in that the bonded atoms share electrons, but the electrons are attracted more strongly to the oxygen nucleus than to the hydrogen nuclei. This creates a small positive charge near the two hydrogen nuclei. Clusters of water molecules form because the positive charges of the hydrogen atoms are attracted to the negative charge of the oxygen atoms from other water molecules. It is well known that such hydrogen bonds play important roles in many biological compounds, and is essential for maintaining the shape or large molecules such as proteins and nucleic acids.

The pattern or clustering of water is evidenced by the ability to photograph a crystal formed by the water. A crystal is a solid substance with orderly-configured atoms and molecules. In addition to being in snow and crystallized quartz, crystals are also seen in natural minerals such as diamonds and table salt. When a water molecule crystallizes, pure or "natural" water becomes pure crystal, but contaminated, chemically treated "dead" water may not crystallize in the natural tetrahedron. Water treated by the present invention crystallizes in the same manner as "natural" water.

The vortex is a universal background of nature. Vortices deliver energy and are tools that nature uses to assemble and disassemble its creations. Vortices form matter, shape it and hold it together. They guide processes by centripetally charging and feeding growth and then centrifugally discharging it and throwing it back to death or non-motion. A vortex is an orderly, consistent, regenerating technology.

Vortices exist in water such as in creeks, rivers, or in the air. Within every stream, water constantly circles in small vortices called eddies. The same movement is seen in the waves of the ocean constantly rolling in spiral movements. This motion causes water to gather electrical force. Water stores this potential energy. The centripetal, inward-directed movement of water causes it to become rejuvenated.

Implosion causes matter to move inwardly. This inward (centripetal) motion does not follow a straight path to the center, but a spiraling whirling path—a vortex. The outside of the vortex moves slowly and the center moves much more quickly. As water is imploded, suspended particles, which are denser than water are sucked into the center of the flow, frictional resistance is reduced and the speed of the flow increased. Changes of the chemical properties in the water have been reported, including changes of the oxygen content, surface tension is reduced, and the precipitation and bonding of metal ions has occurred.

Thus, there is a need for a method and device for erasing the memory of polluted water, and changing the water's EMF signature from that of the pollutant to that of natural water.

Prior art devices have demonstrated some ability to modify the quality of water to some degree. Most have employed a ring or horseshoe shaped magnet to fit over the outside of the plumbing to affect the polarization of the water molecule. Others have employed D.C. current wire coils to offset the same outcome. A few have inserted D.C. electrodes into the water cavity to modify the quality of the water. Others have used a high voltage electric discharge to produce ozone in a closed chamber with resulting gas being injected into the water flow thus sterilizing the water.

That some magnetic treatments of water can have lasting effects on water is known. X-ray crystallography and electron microscopy have been used to examine scale formed by hard water. The scale formed by untreated water and by magnetically treated water is different. There is a difference in the scale from the treated and untreated water, which extends for at least several days.

For example, CEPI-CO, of Belgium has sold hundreds of thousands of its anti-magnetic water treatment to reduce scaling in industrial cooling circuits. These magnetic water treatment units are in continuously recirculating systems and are solely for the purpose of scale suppression. Nevertheless, their useful results prove that magnetic treatment of water can have lasting beneficial effects and can cause changes in the water's crystallization behavior. These results have only been obtained via dynamic magnetic treatment, i.e. the fluid moving rapidly through an orthogonal magnetic field to produce semi-permanent changes in the water.

Further, magnetic fields are also known to reduce the surface tension and viscosity of water. Studies have shown that magnetic treatment of water can alter the effectiveness of certain types of bacterially mediated oxidation of pollutants.

The instant invention likewise non-chemically treats water in a way that imparts a beneficial memory, or semi-permanent effect, of the treatment to the water.

There are previous apparatus for magnetically treating fluid. The magnetic field is normally applied axially by winding an electromagnetic coil about a tube or vessel through which the fluid is passed. Thus efficiency is poor as the applied voltage is increased near the magnets, and decreased in the center of the tube. The field strength is non-uniform, and as a result is ineffective.

U.S. Pat. No. 3,873,448: This invention is described as "a magnetic separator having particular utility in separating ferromagnetic materials with sizes on the order of microns from viscous fluids". The separator utilizes a ferromagnetic filler in the form of a bed of ferromagnetic particles through which the fluid is passed. The magnetic field established in the filter extends transversely to the direction of fluid flow. Electromagnetic coils in a position relative to electromagnets cause the field. The invention further required flushing when the filter medium is filled with particles. In addition the DC potential on the coil, must be then changed to an AC potential. This caused demagnetization of the particles forming the filler. The filter medium is described as "steel shot or other particles constituting filter," and as a layer of seven inches thickness of one-sixteenth Inch stool shot" in this design. There is no reference to the significance of the round balls of the steel shot, and the patent appears to only use it as a filter that can be magnetized. While this invention does include round steel shot as a filter, its purpose is as a separator of ferromagnetic materials.

U.S. Pat. No. 4,836,932: This invention uses a "water treatment cell" producing locally strong "super magnetic fields (60,000 to 250,000 Gauss)." This is accomplished when minute highly intense magnetic fields are produced, with stabilization of micro-magnet geometry. These fine particles are dispersed in nonmagnetic media. This "super magnet" is then placed in a vessel for treating the water. Minerals such as ionized calcium in the water precipitate our as calcium powder at the bottom of the vessel. This technology is primarily used to separate waste materials from the water. In addition a turbulent flow is required, but may need to be adjusted. The invention's intended use is in a recirculating system for descaling. No round balls or magnets are used, and the water is passed into a vessel containing these super magnets.

U.S. Pat. No. 3,869,390: This mechanism is an electromagnetic filter for removing iron oxide from the food water of boilers in steam power plants. It includes a filter bed of metal balls in a vessel with an excitation coil located about the vessel. The coil has passages for cooling and a jacket allows for openings for the cooling medium. The magnetic field is produced outside the balls. This device is a filter that requires DC and AC current, and is limited to a specific use.

U.S. Pat. No. 4,501,661—This invention claims to provide a method and apparatus for purifying and activating water, to obtain natural-like water being fungi-free clean and rich in taste and minerals. The devise consists of three chambers. 1. The first a deceleration zone using an agent in porous granular form with an ability to decompose combined chlorine and absorbs free chlorine, such as calcic ceramic (obtained from shells of shellfish and treating them at ultrahigh temperature. 2. The second chamber is an activation zone where water is disordered with its equilibrium state and ionized. The water will be neutral or weal-alkaline in this zone. This is accomplished by using charged particles of Elvan (magnetic multielementary mineral and magnet bars installed longitudinally among said particles. 3. The third chamber, the settlement zone is to disturb the ionic balance of water and orient it to be softened. This chamber contains a magnet ball of acrylic resin, which contains a magnetic pellet in its free space. The number of balls could be as few as three. This devise is complex, contains many mediums of treatment, and does not use the magnetic balls for flow or direction, but only as a source of a magnetic field. The magnetic field is not claimed to dechlorinate, as a medium is claimed to accomplish that in the first chamber. The use of magnetic balls is not comparable to the present invention.

U.S. Pat. No. 4,904,381—This device is an apparatus for magnetization treatment of fluid by having a rotor with a magnetic field generator rotatably in a passage or reservoir of fluid, and a rotating means coupled to the rotor. Treatment is effected by a magnetic field generator, which is rotated integrally to generate a rotating magnetic field in its surroundings. Again, a filter member is applied to the water in a chamber containing small balls formed of a permanent magnet and gold or silver-plated. Each produces a static magnetic field against the water and narrow gaps serve to remove impurities contained in the water. The inventor states that the filter member need not be limited to round ball magnets, but might be of ceramics containing Ca, Mg and other elements effective for drinking water and agricultural products. The magnetic field generator comprises a plurality of permanent magnets. An air suction pipe is provided to increase water flow rate, producing bubbles to increase oxygen content of water. The filter member, round magnet balls, is used remove impurities not to treat the water. Water treatment and changes occur due to the magnetic field generator rotating in the first chamber.

SUMMARY OF THE INVENTION

The present invention includes a structure that introduces rapidly spinning vortices in the fluid. The vortices prepare the fluid to have memorized EMF signatures of harmful materials erased, and a new, desirable signature introduced. The present invention further incorporates a means for adding a desirable frequency to the fluid. This may be accomplished by many different means, including those embodiments disclosed herein.

The present invention provides a novel apparatus that will treat water, or other fluids, in a manner that returns them to their natural states.

Further objectives of the present invention are:
a. To provide for treatment of polluted water and fluids.
b. To reduce or eliminate the need for chemical sanitizers such as chlorine, bromine, stabilizers, algaecides, and clarifiers in swimming pools, spas, cooling towers, municipal and other water systems.

c. To treat water such that it has a greater absorption rate in the body of an animal, and thus, is capable of increasing the delivery of nutrients from food, nutritional supplements, and medicines and pharmaceutical products.

d. To increase penetration and cellular hydration of cosmetics and skin care products.

e. To reduce or eliminate the need for pesticides, herbicides, and fertilizers in agricultural processes.

f. To provide treatment of other fluids to provide clusters to make them more efficient and effective.

g. To reduce surface tension. the present invention are measurable. The surface tension of water is lowered from 72 dynes to 62 per centimeter. (Dyne is a unit of measurement used to describe the permeability of a liquid.)

h. To retard growth of algae, bacteria, and fungus in water.

i. To increase electrical conductivity.

j. To establish hydrogen bonding. Water is either structured or unstructured, dependant upon whether or not hydrogen bonding connects clusters of water molecules together or not. Water that is structured with hydrogen bonding will have a more balanced pH.

Under normal conditions, natural clustering or water molecules is short lived and the cluster size is unpredictable. The present invention changes the cluster pattern of the water or other fluids, causing change to be long lasting. Water which has been treated to have a more ordered and stable structuring of water molecules has been produced by other inventions using magnetic treatment of the water, but none bas imparted a new pattern or cluster to the water, thereby, they have been unable to "hold" the change in the water. They do not complete the process needed to remove the negative programming and impart new programming, thereby semi-permanently changing the water.

The present invention will remove the negative "frequencies or programming," structure the water to receive a new program, and impart that program to the water. This process will cause the improvements in the water to be longer lasting, without constant recirculation of the water through the devise.

It is anticipated that the present invention will be useful for industries such as: municipal water treatment, pool and spas, hotels and restaurants, air conditioning, agriculture, cosmetics, food and beverages.

Further, biologically active fluids such as raw milk, raw wine, juices, and other fluids can have their shelf life extended by reducing the amount of live bacteria in them. Ultra pasteurization of milk, for example, produces milk with a long shelf life. One aspect of the invention is to similarly use the described structure and process to reduce the amount of such potentially harmful bacteria in the treated fluid.

Additionally, however, fluids treated by the described structure and process subsequently resist degradation and subsequently retard or prevent the growth of new bacteria which is introduced into the treated fluid compared to untreated fluids. For example, ultra pasteurized milk will resist degradation for a long period of time because the ultra pasteurization greatly decreases the amount of bacteria in the milk. Once the ultra-pasteurized milk is opened and is exposed to new bacteria, however, it quickly spoils. Milk treated with the present invention, however, is less hospitable to newly introduced bacteria and, consequently, has a longer shelf life after being exposed to new bacteria than does ultra pasteurized milk.

These two benefits, first the reduction in the amount of bacteria in the treated fluid, and second the long lived conditioning of the fluid to subsequently resist the reintroduction of the bacteria to grade the fluid, are effects that are also useful in biodegradable fluids other than milk.

Treated fluid produced by the process can be used to either improve or to adversely affect living organisms depending on the amount and concentration of treated fluid that is applied. Highly treated water can be used to kill plants, microorganisms, and undesirable life. Treated fluid which is subjected to a lesser amount of treatment can be used to improve the health of plants, microorganisms, and other undesired life. For example, cut flowers placed in treated water last longer. Further, potted flowers treated with an appropriate amount of treated water will grow faster, but if the concentration of treated water is too much, then the growth of the plants is retarded.

Among other effects, the present invention has been measured to reduce the surface tension of tap water from 72 to 62 dynes per centimeter.

The semi-permanent nature of the described effects makes the treatment useful for pools, municipal water supplies, and the like.

DETAILED DESCRIPTION OF THE PREFERRED EMBODIMENT

Figure 1:
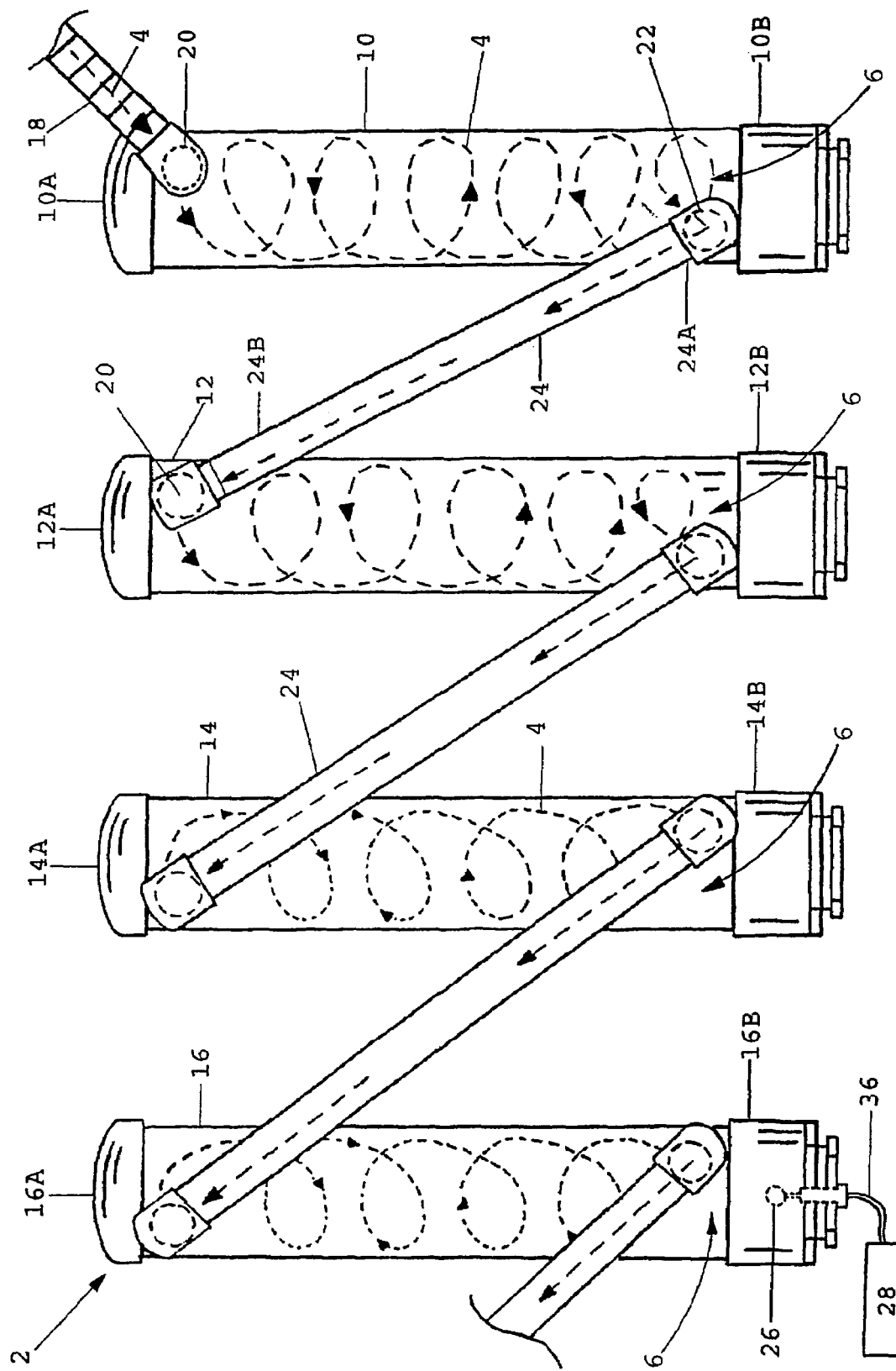
FIG. 1. is a side view of a first embodiment of the present invention.

Referring to the figures, FIG. 1. shows a side view of a first embodiment of the present invention. The fluid treatment apparatus (2) incorporates two or more vortex chambers (10, 12, 14, and 16) in which a vortex (6) is created. As shown in FIG. 1., a first embodiment of the fluid treatment apparatus (2) uses four vortex chambers (10, 12, 14, and 16) that are substantially tubular in shape, that is, a cylinder with an aperture extending along the longitudinal axis of the cylinder. However, it is anticipated that most variations of the first embodiment of the fluid treatment apparatus (2) will contain two to ten vortex chambers (10, 12, 14, and 16). The vortex chambers (10, 12, 14, and 16) are connected together in series with a fluid inlet (20) in the first vortex chamber to allow for entry by fluid (not shown) into the vortex chambers (10, 12, 14, and 16) from a fluid source (not shown). Fluid (not shown), generally water (not shown), travels through the fluid entry tube (18) and enters the first vortex chamber (10) near a first end of the first vortex chamber (10a). The fluid (not shown) travels from the first end of the first vortex chamber (10a) downwardly to the second end of the first vortex chamber (10b), where it exits from the first vortex chamber (10) through a fluid outlet (22). The fluid (not shown) then travels through a connection tube (24) which is connected at a fluid connection tube first end (24a) to the fluid outlet (22), and connected at a fluid connection tube second end (24b) to a fluid inlet (20) near a second vortex chamber first end (12a). The fluid (not shown) again travels downwardly through the second vortex chamber (12) where it exits a fluid outlet (22) near the second vortex chamber second end (12b). The fluid (not shown) continues traveling through the third vortex chamber (14) and the fourth vortex chamber (16), or until it has reached the last of the vortex chambers (not shown), if more than four, in the series and exits through a final fluid outlet (22).

The fluid inlets (20) and fluid outlets (22) are sized and positioned in order to maximize the fill characteristics of the fluid (not shown) in the fluid treatment apparatus (2), as well as to increase the vortices (6) created within the vortex chambers (10, 12, 14, and 16). The diameters of the vortex chambers (10, 12, 14, and 16) and the inlets and outlets can be changed, but it is generally done proportionally. It has been found that a desirable ratio of fluid inlet (20)/fluid outlet (22) diameter to vortex chamber diameter ratio is in the range of ⅔ to ⅙. Therefore, if the vortex chambers (10, 12, 14, or 16) were 4 inches in diameter, the fluid inlet (20), fluid outlet (22), and connection tube (24) would be approximately 1½–2 inches in diameter. The diameters can be changed proportionally.

For example, pool water or municipal water may be treated in accordance with the above specification, and scaled up or down as needed depending upon the volume of the water (not shown) to be treated, the expected time period between treatments, and the extent to which the water (not shown) is polluted. The fluid treatment apparatus (2) will more benignly kill biological active components of the treated fluid (not shown) than other methods of killing such biological active components. Heavy chlorination, a sufficiently intense magnetic field, and sufficient pressure will all kill bacteria. However, the present invention kills bacteria more economically and with semi-permanent effects, in other words, water (not shown) treated by the present invention resists reinfection by biological contaminants such as bacteria, algae, and fungi.

The forth vortex chamber (16) also has a frequency antenna (26) attached inside the forth vortex chamber (16). The frequency antenna (26) is located near the forth vortex chamber second end (16b) near the level of the fluid outlet (22). The frequency antenna (26) is connected to a frequency antenna generator (28) by means of a frequency lead (36).

The fluid treatment apparatus (2) is used in conjunction with a fluid system (not shown) that can be comprised of many types of fluid transport systems (not shown), such a pipelines (not shown) or a simple fluid container (not shown). As used herein, a fluid system (not shown) is intended to include any source or means that supplies fluid to the fluid treatment apparatus (2).

The fluid treatment apparatus (2) can be comprised of any number of vortex chambers (10, 12, 14, and 16), but is generally made up of 2 to 10 vortex chambers (10, 12, 14, and 16) inside which vortices (6) are created. The vortex chambers (10, 12, 14, and 16) are connected together in series with a fluid inlet (20) for the first vortex chamber (10) from the fluid source (not shown). The fluid outlet (22) from the first vortex chamber (10) is connected to the fluid inlet (20) of the second vortex chamber (12), and all vortex chambers (10, 12, 14, and 16) are connected in similar fashion.

The fluid inlet (20) may be positioned at an angle, often in the range of 8–15 degrees, to improve the flow characteristics of the fluid (not shown) and increase the power of the vortices (6). The fluid outlet (22) may be angled as well.

Figure 2:
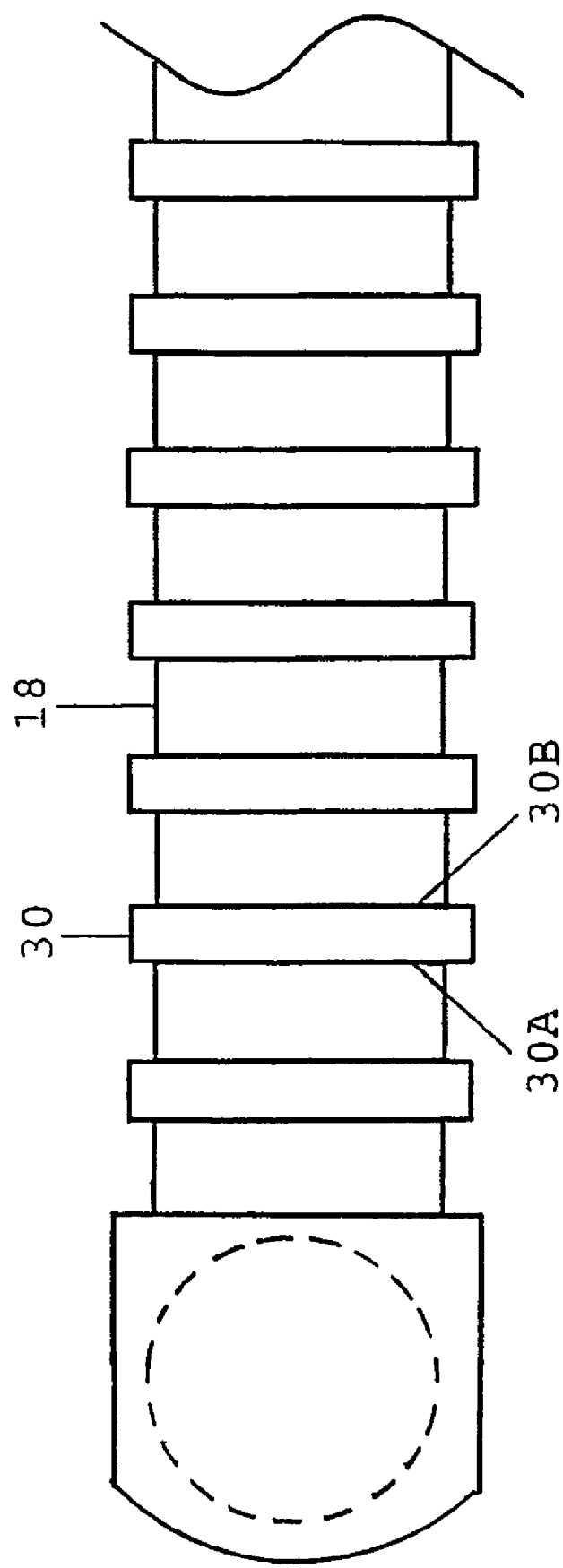
FIG. 2. is a side view of the fluid entry tube of a first embodiment of the present invention.

FIG. 2. is a side view of the fluid entry tube (18) of a first embodiment of the present invention. The fluid entry tube (18) is in communication with a fluid system (not shown), or fluid source (not shown), and is attached to the fluid inlet (20) of the first vortex chamber (10). The fluid entry tube (18) allows fluid (not shown) to enter the treatment apparatus (2). The fluid entry tube (18) may have a polarity of magnetic rings (30) associated with it. The magnetic rings (30) are attached to, and circumscribed, to the fluid entry tube (18). It is intended to the magnetic rings (30) may be of relatively strong magnetic force. For example, it is advantageous that each of the magnetic rings (30) be of a gauss strength of 5000 or more. The magnetic rings (30) are polarized and have a positive polarity end (30a) and a negative polarity end (30b). The polarity of magnetic rings (30) are positioned relatively near to each other along the fluid entry tube (18), and oriented such that the polarity ends of any one magnetic ring (30) are closest to the like end of the magnetic rings (30). Thus, positive polarity ends (30a) are next to other positive polarity ends (30a), and negative polarity ends (30b) are next to other negative polarity ends (30b). While other numbers and placements of the magnetic rings (30) may be useful, it is anticipated that the fluid treatment apparatus (2) would incorporate 3–10 magnetic rings (30) located ½ inch to 5 inches apart. For example, the fluid entry tube (18) may be encircled by seven magnetic rings (30) of a Gauss strength of 5000 or more, positioned an inch apart. The inner diameter of the magnet rings (30) is equal to the outer diameter of the fluid entry tube (18).

Figure 3:
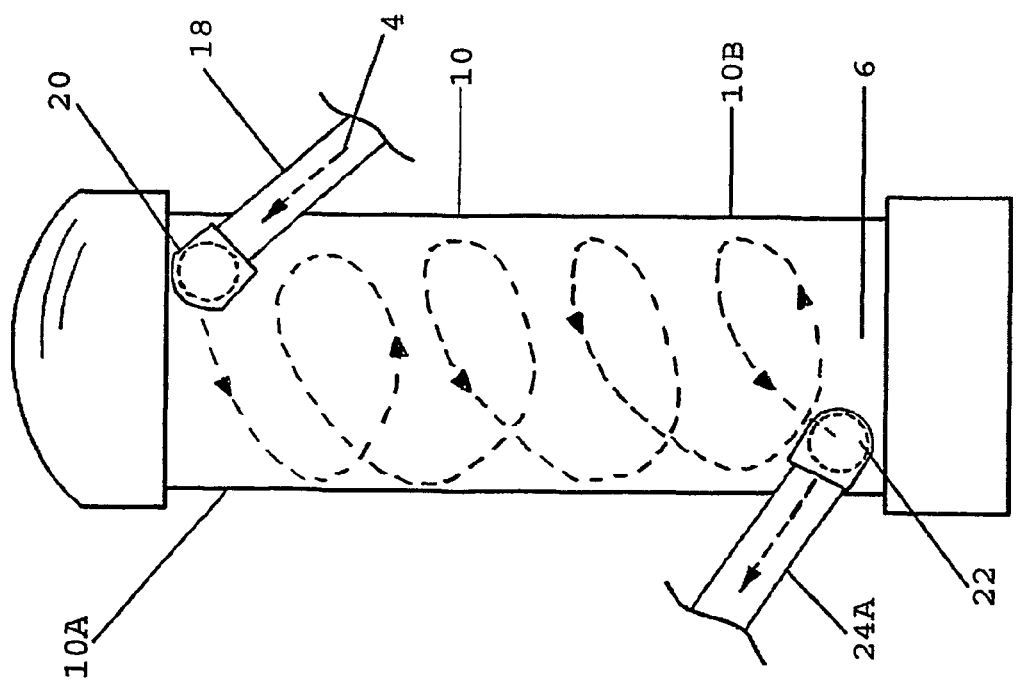
FIG. 3. is a side view of a left spin vortex chamber of a first embodiment of the present invention.

FIG. 3. is a side view of the first vortex chamber (10) of the first embodiment of the present invention. It illustrates the direction of the water flow (4) within the first vortex chamber (10). As shown, water (not shown) enters the first vortex chamber (10) through the fluid inlet (20) and exits through the fluid outlet (22). The positions of the fluid inlet (20) and the fluid outlet (22) are such that the fluid flow (4), and the resulting vortex (6), are in a left spin orientation or counterclockwise rotation. Water (not shown) fills the first vortex chamber (10), but the exit of the water (not shown) creates the vortex (6). The main vortex (6) extends lengthwise along the center of the interior of the first vortex chamber (10). The makeup of a vortex (6) is such that multiple, smaller vortices create the main vortex (6). At the bottom of the vortex (6), the energy of the water (not shown) is at its highest. This point is the chaos point (not shown) or apex (not shown) of the vortex (6). At the chaos point (not shown), the strands of water (not shown) have the tendency to turn in the opposite direction that they were spinning in the vortex (6). Thus, the water (not shown) that has passed through a counterclockwise vortex (6) will tend to want to spin back clockwise at the chaos point (not shown).

The second vortex chamber (12) is described by FIG. 3.

Figure 4:
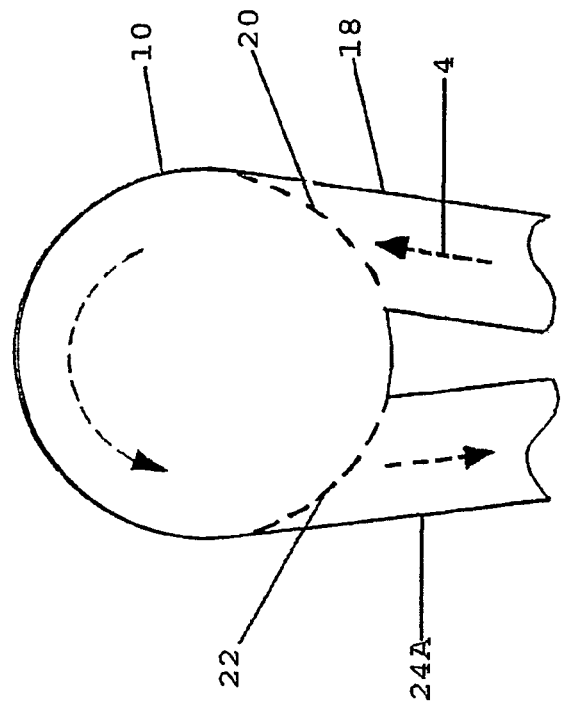
FIG. 4. is a top view of a left spin vortex chamber of a first embodiment of the present invention.

FIG. 4. is a top view of the first vortex chamber (10). It illustrates water flow (4) entering from a fluid entry tube (18) through the fluid inlet (20) and creating a counterclockwise vortex (6) as indicated. The water (not shown) then exits through the fluid outlet (22) and into a connection tube first end (24a).

Figure 5:
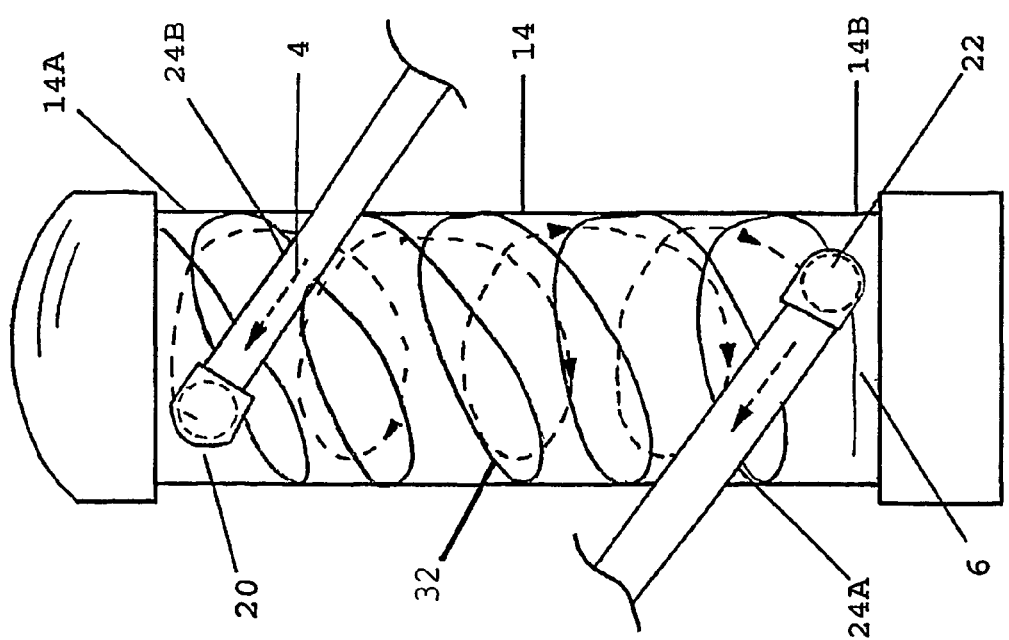
FIG. 5. is a side view of a right spin vortex chamber with a copper coil of a first embodiment of the present invention.

FIG. 5. is a side view of a third vortex chamber (14). The third vortex chamber (14) operates in the same manner as described for the first vortex chamber (10) in FIGS. 3. and 4., except that the fluid inlet (20) and fluid outlet (22) are arranged such that the vortex (6) created has a right spin or clockwise rotation. Additionally, a copper coil (32) is contained within the third vortex chamber (14). It is coiled in the same direction as the vortex (6) is designed to spin. While the first vortex chamber (10) and the second vortex chamber (12) are designed to "erase" memory from the fluid (not shown), the presence of the copper coil (32) allows desired frequency from the copper to resonate through the water (not shown). This imparts memory upon the water (not shown) to create a permanent change in the water (not shown), known as clustered water (not shown). Copper is known to have algaecide and fungicide properties. As the water (not shown) passes across these metals, a frequency or "memory" is imparted that structures the water (not shown).

Copper ions are also transferred to the water (not shown) by the process of galvanic corrosion, giving it the additional advantage of containing ions that directly combat algae and fungi. Galvanic corrosion occurs when dissimilar conducting materials are connected and exposed to an electrolyte. This causes the metals to assume different corrosion potentials. It is this potential difference that is the driving force for galvanic current flow. In this invention, copper becomes an anode and silver will act as a cathode, while water (not shown) is the electrolyte.

Figure 6:
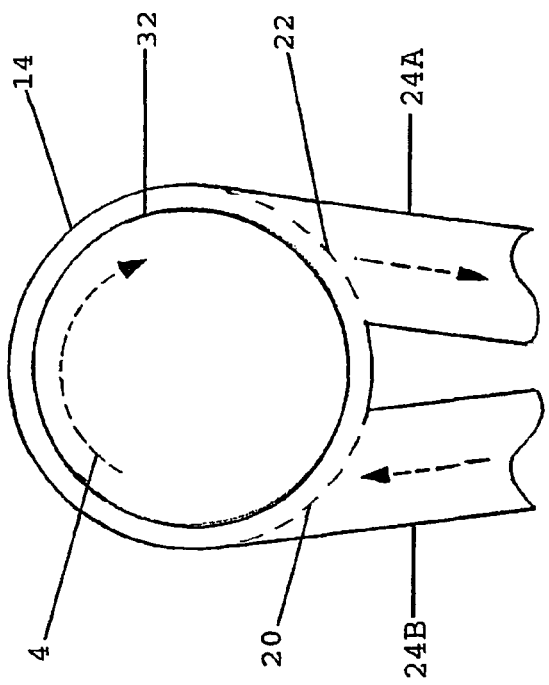
FIG. 6. is a top view of a right spin vortex chamber with a copper coil of a first embodiment of the present invention.

FIG. 6. is a top view of the third vortex chamber (14). Like FIG. 4. it illustrates the fluid flow (4) of the water (not shown). Unlike FIG. 4., the fluid flow (4) of the third vortex chamber (14) is clockwise or to the right. The copper coil (32) is also illustrated in FIG. 6., resting inside the third vortex chamber (13).

Figure 7:
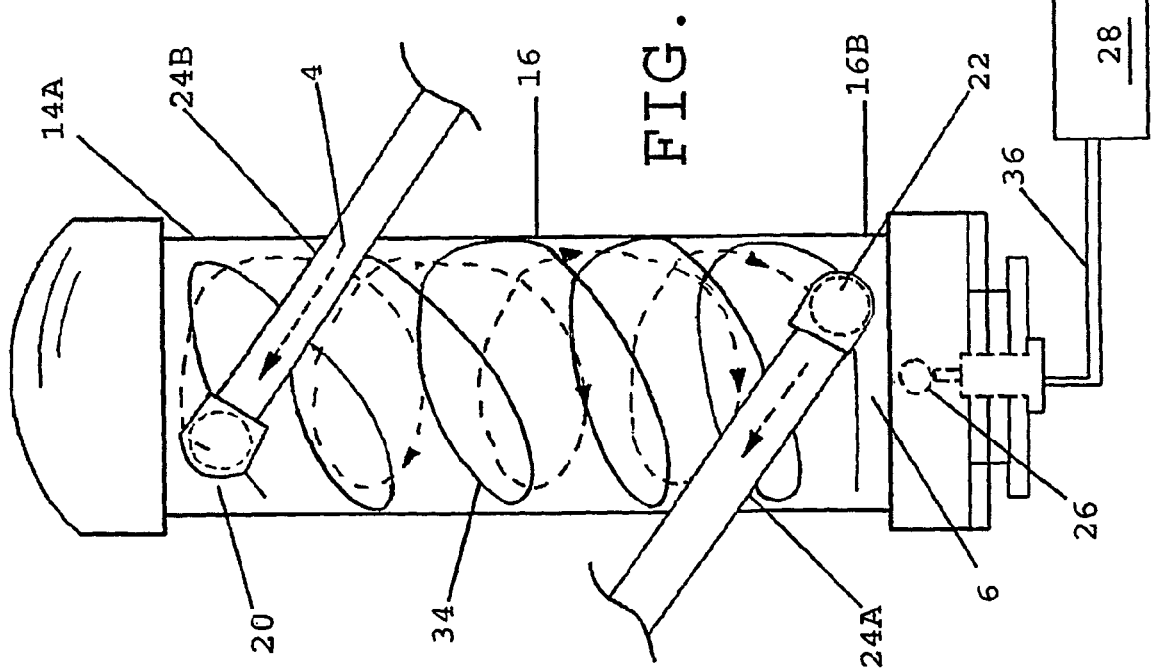
FIG. 7. is a side view of a right spin vortex chamber with a silver coil and a frequency antenna of a first embodiment of the present invention.

FIG. 7. is a side view of the fourth vortex chamber (16). The forth vortex chamber (16) and the fluid flow (4) illustrated in FIG. 7. are virtually identical to that of the third vortex chamber (14) and FIG. 5. The fourth vortex chamber's (16) fluid inlet (20) and fluid outlet (22) are positioned in the same manner as the third vortex chamber (14) causing the fluid (not shown) to create a vortex (6) that rotates to the right, or clockwise. The forth vortex chamber (16) also has a coil, but a silver coil (34) is inserted in place of the copper coil (32). Again, the silver coil (34) is coiled in the same direction as the intended spin of the vortex (6). As with the copper coil (32), the silver coil (34) imparts memory upon the water (not shown) to create a permanent change in the water (not shown), known as clustered water (not shown). Silver is a bactericide. As the water (not shown) passes over the silver coil (34), a frequency or "memory" is imparted that structures the water (not shown). Silver ions are also transferred to the water (not shown) by the process of galvanic corrosion, giving it the additional advantage of containing ions that directly combat bacteria.

At the fourth vortex chamber second end (16b) a frequency antenna (26) is attached. The frequency antenna (26) is placed in the center of the forth vortex chamber (16). It is placed at a height such that the frequency antenna (26) is suspended near the chaos point (not shown) of the vortex (6). The frequency antenna (26) is in communication with a frequency generator (28) by means of a frequency lead (36). The frequency generator (28) supplies power to the frequency antenna (26). The frequency lead (36) may be a single lead connected to the frequency generator (28) with no ground lead provided. In this case, the electrical circuit between the frequency antenna (26) and the frequency generator (28) is not complete. The power that is passed to the frequency antenna (26) has a variable frequency of up to 1000 Hertz. Thus, frequency is released into the water (not shown) at the bottom of a vortex (6) near the chaos point (not shown).

Figure 8:
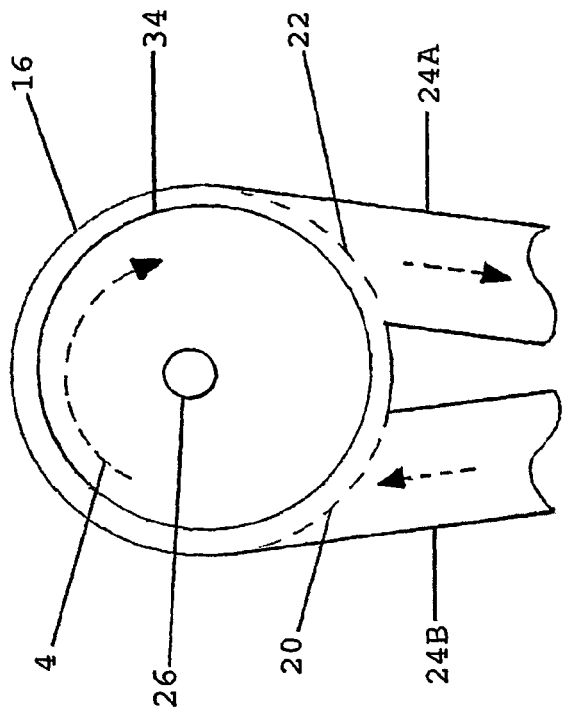
FIG. 8. is a top view of a right spin vortex chamber with a silver coil and a frequency antenna of a first embodiment of the present invention.

FIG. 8. is a top view of the forth vortex chamber (16). It is identical to FIG. 6. in all respects except that the silver coil (34) is illustrated in place of the copper coil (32) and the frequency antenna (26) is present in the center of the fourth vortex center (16).

Figure 9:
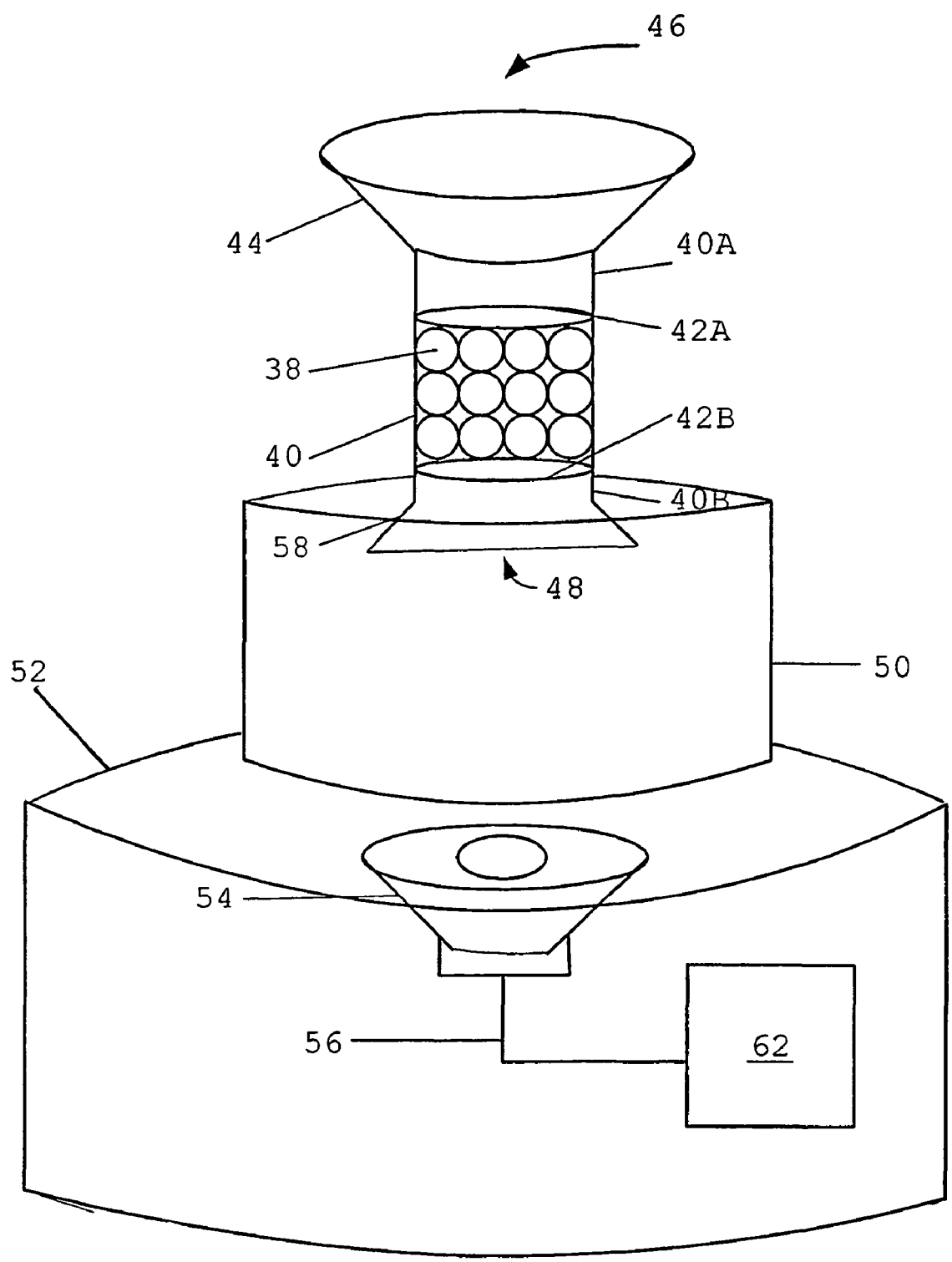
FIG. 9. is a side view of a second embodiment of the present invention.
Figure 12:
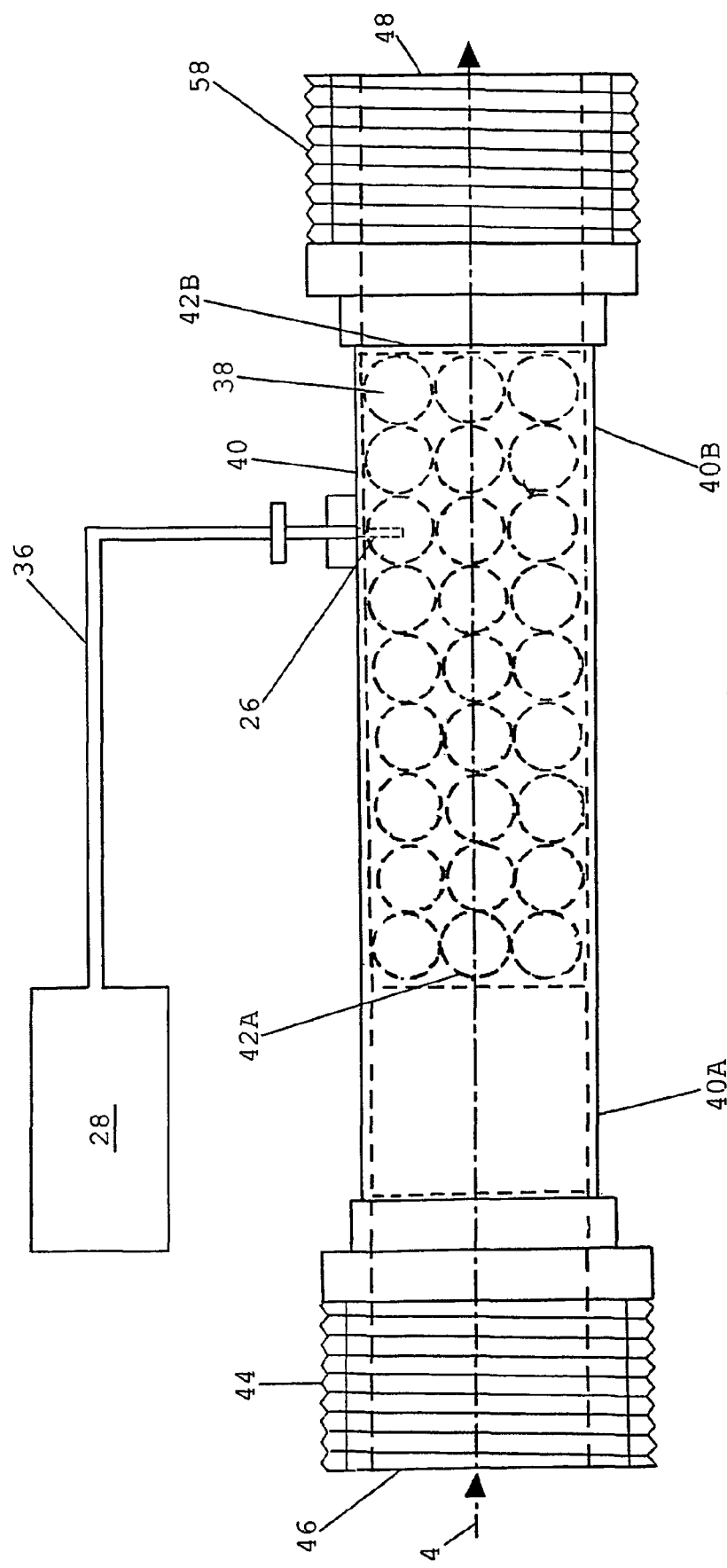
FIG. 12. is a side view of a third embodiment of the present invention.

FIG. 9. is a prospective view of a second embodiment of the present invention. It illustrates an alternate embodiment of the present invention that incorporates the same features as the same embodiment. Like the first embodiment, the second embodiment incorporates a fluid system (not shown), or fluid source (not shown) with a vortex creation apparatus and a frequency generation device. The main differences between the various embodiments are in the forms that the vortex creation apparatus and the frequency generation device take. While the first embodiment of the vortex creation apparatus took the form of a series of vortex chambers (10, 12, 14, and 16), and the frequency generation device took the form of metallic coils (32 and 34) and a frequency antenna (26), the second embodiment uses different forms for the vortex creation apparatus and frequency generation device. The second embodiment as illustrated in FIG. 9., uses a vortex chamber member (40) with a first end (40a) and a second end (40b). The vortex chamber member (40) is substantially tubular in shape. Water (not shown) enters enter the vortex chamber member (40) through a first aperture (46). The fluid (not shown) flows through the vortex chamber member (40) and exits through a second aperture (48). Attached to the vortex chamber member first end (40a) is a fluid entry piece (44). The fluid entry piece (44) can take different forms. FIG. 9. illustrates and embodiment wherein the fluid entry piece (44) is substantially a frontal that allows fluid (not shown) to be poured into the vortex chamber member (40) more easily. This allows the present invention to be used on the "table-top" with a user pouring water (not shown) or other fluid (not shown) into the vortex chamber member (40). As shown in FIGS. 12., 13., and 14., the fluid entry piece (44) can also be threaded in order to allow the vortex chamber member (40) to be inserted into a pipe line (not shown) or other fluid system (not shown). Also attached to the vortex chamber member (40) at the vortex chamber second end (40b) is a fluid exit piece (58). Like the fluid entry piece (44), the fluid exit piece (58) can take various forms, including but not limited to, the threaded versions shown in FIGS. 12., 13., and 14.

The vortex creation apparatus of the present invention, regardless of the embodiment, is designed to create vortices (6) in the fluid (not shown). In the second embodiment shown in FIG. 9., the vortices (6) are created by a series of rows of micro-spheres (38). The plurality of micro-spheres (38) are held within the vortex chamber member (40) by use of a first strainer (42a) and a second strainer (42b). The first strainer (42a) is attached to the interior of vortex chamber member (40) near the vortex member first end (40a). The second strainer (42b) is attached to the interior of the vortex chamber (40) near the vortex chamber member second end (40*b*). Both the first strainer (42*a*) and the second strainer (42*b*) are designed such that fluid (not shown) can pass through, but the micro-spheres (38) can not. Although not shown, the fluid entry piece (44) and the fluid exit piece (58) can also be formed in order to act as the first strainer (42*a*) and the second strainer (42*b*).

Water (not shown) that is passed through the vortex chamber member (40) is collected in a fluid container (50) or passed on into the continuing fluid system (not shown). The fluid container (50) rests on a base member (52). Within the base member (52) there is a transducer (54) connected by a power lead (56) to a power supply (62). An example of this mechanism is using an audio speaker, which is a type of transducer, to supply the frequency. Thus, in this second embodiment, the transducer (54) acts as the frequency generation device. It passes audio waves up through the fluid (not shown) that is held in the fluid container (50) and parting frequency on the fluid (not shown).

In order to accept the desired frequency, the fluid (not shown) must have passed through vortices (6) sufficient to erase any unwanted frequencies. The micro-spheres (38) act as the vortex creation apparatus in the second embodiment. As the water (not shown) flows in between the spaces of the micro-spheres (38), it is subjected to intense turbulence and many vortices. These vortices act to erase memory from the water (not shown) and prepare it to accept the frequencies generated by the transducer (54). The audio frequency of the sound emitted from the transducer (54) is generally in the range of 300 to 1500 Hertz.

Figure 11:
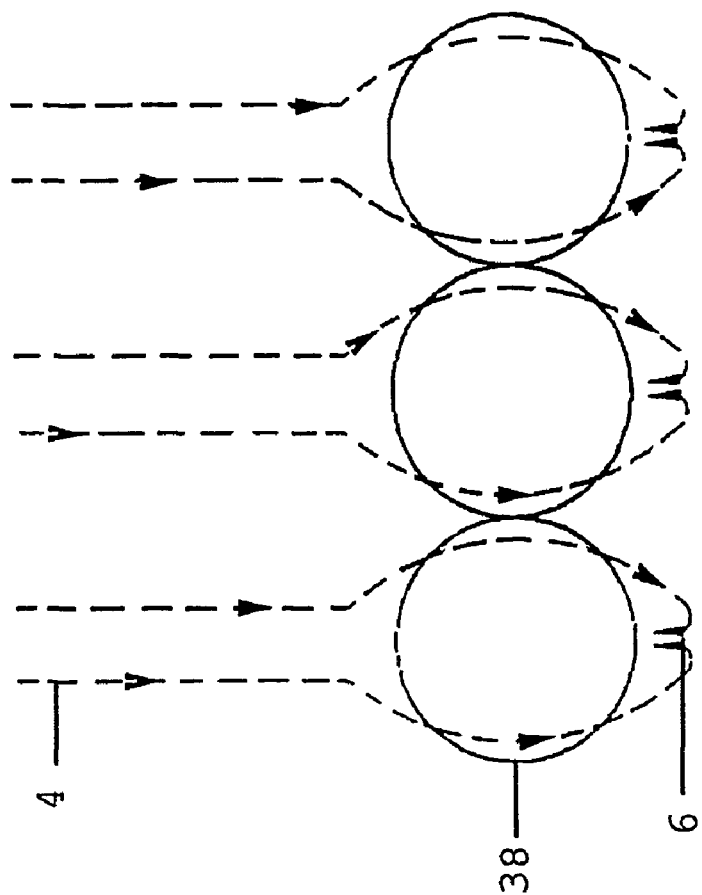
FIG. 11. is a schematic illustrating fluid flow about the micro-spheres of the present invention.
Figure 10:
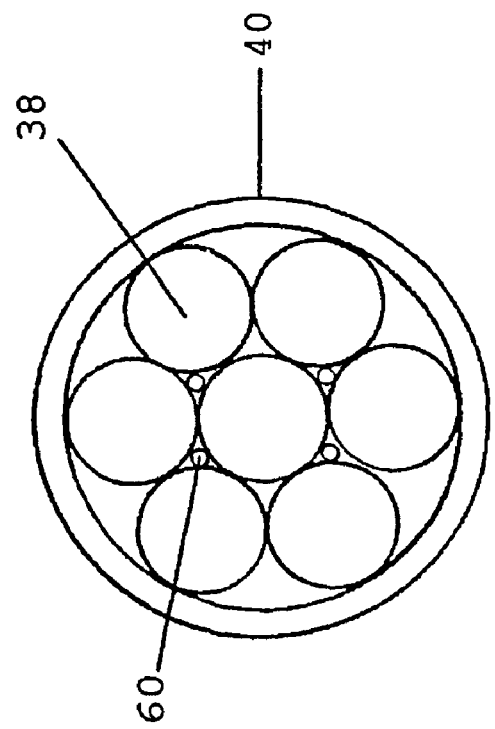
FIG. 10. is a cross-sectional view of the micro-spheres taken along axis X—X of FIG. 9.

FIG. 10. is a top, cross-sectional view of the micro-spheres (38) taken along plane X—X of FIG. 9. As the fluid (not shown) between the spaces created by the micro-spheres (38), it is subjected to intense turbulence and vor-texing as shown in FIG. 11. The micro-spheres (38) may be magnetic with high Gauss ratings, often at least 3500. The polarity of magnetized micro-spheres (38) creates a complex, alternated magnetic field formed with all of the micro-spheres (38) acting collectively as one large porous magnet through which all of the fluid (not shown) flows.

In order to ensure creation of the vortices (6) and increase their energy, fluid (not shown) may be passed through the vortex chamber member (40) using relatively high pressure, often at least 20 psi. The pressure allows longer contact with the micro-spheres (38) and a uniformity of exposure. However, such pressure is not required in all cases.

The micro-spheres (38) may be arranged into a plurality of ordered rows, although it is not required. The rows may be organized as illustrated in FIG. 10., with six micro-spheres (38) around the interior of the vortex chamber member (40), and one micro-spheres (38) in the center, if such a formation fits in the vortex chamber member (40). Such a formation is dependant upon the diameter of the interior of the vortex chamber member (40), and the diameters of the micro-spheres (38). The number of micro-spheres (38) in each row and their positioning can be modified to fit the vortex chamber member (40). In those cases were magnetized micro-spheres (38) are used, the micro-spheres (38) will generally orient themselves on their own, based on their polarities.

While FIG. 9. illustrated a second embodiment of the present invention in which a transducer (54) is used to apply frequency. Frequency can also be applied using metallic strands (60) which are similar to the coils illustrated in the first embodiment. A metallic strand (60) is made from either copper or silver in order to impart their beneficial effects on the fluid (not shown).

Any trace mineral salts in the water (not shown) will be polarized upon passing through the terminal, on its way out of the system. This results in the suspension of all material in the water (not shown) due to polarization and the prevention of any deposits (called scaling) being allowed to form on the inside of the fluid system (not shown) as randomly polarized mineral salts can do.

pH is the balance between charges in the water (not shown). Wide variations in pH damage equipment and can reduce the effectiveness of chemicals. By organizing the water (not shown) magnetically the pH will be come more stabilized.

FIG. 11. is a schematic illustrating fluid flow (4) about the micro-spheres (38) of the present invention. It is a side view of the micro-spheres (38) also taken along plane X—X of FIG. 9. The fluid flow (4) travels in a straight path until encountering the micro-spheres (38) at which time it swirls around the micro-spheres (38) with strands of water (not shown) coming together to form micro-vortices (not shown). The micro-spheres (38) rapidly swirl the fluid (not shown) to be treated into many vortices (6) among the high gas magnetic micro-spheres (38). The relatively high pressure on the fluid (not shown) moving it through the vortex chamber member (40) subjects the fluid (not shown) to the effects of the described frequency generation device. The combination of the spherical, small, high gauss magnetic micro-spheres (38), and high pressure passing the fluid (not shown) through the fluid treatment apparatus (2) at sufficient velocity to create vortices (6), act in combination to kill unwanted bio-material. An additional benefit can be the precipitation out of minerals such as iron, calcium, and magnesium, thus helping to prevent scaling.

FIG. 12. is a side view of a third embodiment of the present invention. It is also an alternative embodiment of the vortex chamber (40) in which a frequency antenna (26) is used to impart frequency upon the fluid (not shown) rather than a transducer (54). FIG. 12 shows the vortex chamber member (40) filled with micro-spheres (38). As described above, the fluid entry piece (44) and the fluid exit piece (58) are shown as threaded in order to allow the vortex chamber member (40) to be inserted into a pipeline. Fluid (not shown) still flows through the vortex chamber member (40) along the fluid flow line (4). The frequency antenna (26) is energized by a frequency generator (28) and connected by a frequency lead (26). Frequency is imparted upon the fluid (not shown) in the same manner as described in the first embodiment of the present invention.

Figure 13:
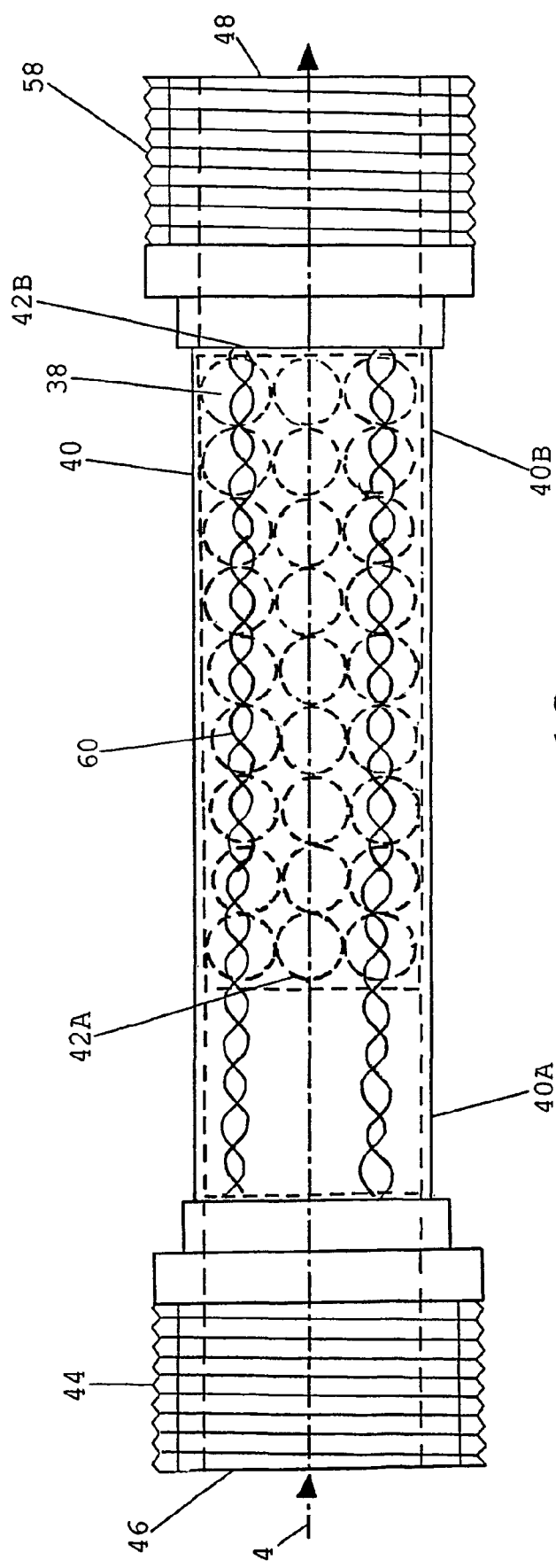
FIG. 13. is a side view of a fourth embodiment of the present invention.

FIG. 13. against shows the vortex chamber (40) with a second alternative means for imparting frequency on the fluid (not shown). While in the first embodiment, copper coils (32) and silver (34) were used, FIG. 13. illustrates metallic strands (60) inserted in the interior of the vortex chamber member (40) along with the micro-spheres (38). Like the copper coil (32) and silver coil (34), the metallic strands (60) are made from desirable metallic substances such as copper or silver. The fluid (not shown) traveling along the fluid flow line (4) is thus subjected to multiple many vortices erasing the memory from the fluid (not shown) while having the beneficial characteristics of the metallic strands (60) imparted on the fluid (not shown).

Figure 14:
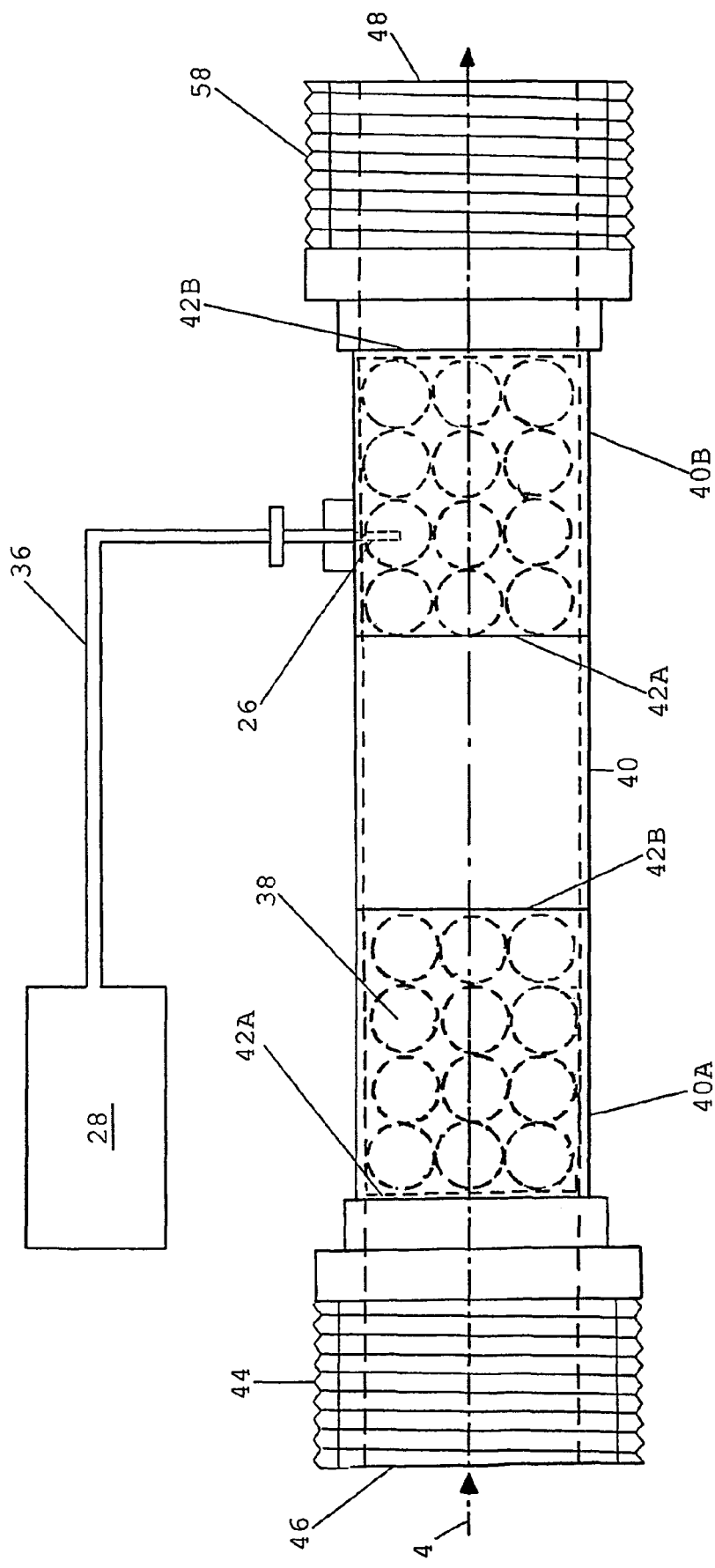
FIG. 14. is a side view of a fifth embodiment of the present invention.

FIG. 14. is a side view of a third alternative embodiment of the frequency generation device for the second embodiment of the present invention. FIG. 14. illustrates a vortex chamber member (40) with two sets of micro-spheres (38). The sets of micro-spheres (38) may be held in place by two sets of first strainers (42*a*) and second strainers (42*b*).

Frequency generation in this alternative embodiment may be done by magnetizing the micro-spheres (38) in one chamber and applying power using the frequency antenna (36) connected by the frequency lead (36) the frequency generator (28) in the other chamber. Thus, fluid (not shown) is structured and existing patterns removed, then desired frequencies applied. The frequency antenna (26) that protrudes into the vortex chamber member (40) imparts positive frequencies upon the fluid (not shown) to create a permanent change. If the fluid (not shown) is water (not shown), the modified water (not shown) is known as clustered water (not shown). The multiple vortices created by the micro-spheres (38) cause a centripetal, inward-directed, movement of the water (not shown). This natural centripetal movement infuses the energy patterns into the water (not shown), causing a long-lasting change.

Although there are many disclosed and possible embodiments of the present invention, they work on the same principle and engage the same method. Each embodiment incorporates a fluid system (not shown), or fluid source (not shown), with a vortex creation apparatus and a frequency generation device. The fluid, generally water, is passed through a plurality of vortices. Generally this is done using a chamber designed to create vortices in the fluid. This is intended to erase the "memory" from biological contaminants from the fluid. It also readies the fluid to "memorize" a new, desirable frequency, which is applied though a number of means such as electricity, audio, and magnetic, using such devices as power leads, speakers, transducers, and magnets. Frequencies from desirable materials can also be applied by contacting the fluid with the material, such as metallic strands of copper and silver. The desirable frequencies make the fluid an inhospitable environment for the biological contaminants, such as bacteria, algae, and fungi, reducing their numbers in the fluid.

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

I claim:

1. An apparatus for treating a fluid comprising: a fluid system; a vortex creation apparatus in communication with said fluid system, said fluid able to flow through said vortex creation apparatus; a frequency generation device in operative engagement with said vortex creation apparatus such that a frequency is applied to said fluid near a chaos point of said fluid, wherein said vortex creation apparatus further comprises:
  a first vortex chamber being substantially tubular in shape, said first vortex chamber having a fluid inlet substantially near a first end of said first vortex chamber and a fluid outlet substantially near a second end of said first vortex chamber, said fluid inlet and said fluid outlet placed so that fluid flowing through said first vortex chamber creates a vortex with a left spin; and
  a second vortex chamber being substantially tubular in shape, said second vortex chamber having a fluid inlet substantially near a first end of said second vortex chamber and a fluid outlet substantially near a second end of said second vortex chamber; said fluid inlet and said fluid outlet placed so that fluid flowing through said second vortex chamber creates a vortex with a right spin.

2. The apparatus of claim 1, wherein said frequency generation device further comprises:
  a frequency antenna attached inside said vortex creation apparatus in contact with said fluid; and
  a frequency lead connecting said frequency antenna to a frequency generator, said frequency generator supplying electricity to said frequency antenna at up to 1000 Hz, and said frequency antenna not electrically grounded such that an electrical circuit between said frequency generator and said frequency antenna is not complete.

3. The apparatus of claim 1 wherein said fluid is water.

4. An apparatus for treating a fluid comprising:
  a fluid system;
  a first vortex chamber being substantially tubular in shape and in communication with said fluid system, said first vortex chamber having a fluid inlet substantially near a first end of said first vortex chamber and a fluid outlet substantially near a second end of said first vortex chamber, said fluid inlet and said fluid outlet placed so that fluid flowing through said first vortex chamber creates a vortex with a left spin;
  a second vortex chamber being substantially tubular in shape and in communication with said fluid system, said second vortex chamber having a fluid inlet substantially near a first end of said second vortex chamber and a fluid outlet substantially near a second end of said second vortex chamber, said fluid inlet and said fluid outlet placed so that fluid flowing through said second vortex chamber creates a vortex with a right spin; and
  a frequency antenna attached inside said second vortex chamber in contact with said fluid.

5. The apparatus of claim 4, further comprising:
  a frequency lead connecting said frequency antenna to a frequency generator, said frequency generator supplying electricity to said frequency antenna wherein said frequency antenna is not electrically grounded such that an electrical circuit between said frequency generator and said frequency antenna is not complete.

6. The apparatus of claim 4, further comprising:
  a metallic coil made from silver or copper in said second vortex chamber.

7. An apparatus for treating water comprising:
  a water source;
  a first vortex chamber being substantially tubular in shape and in communication with said water source, said first vortex chamber having a fluid inlet substantially near a first end of said first vortex chamber and a fluid outlet substantially near a second end of said first vortex chamber, said fluid inlet and said fluid outlet placed so that water flowing through said first vortex chamber creates a vortex with a left spin;
  a second vortex chamber being substantially tubular in shape and in communication with said water source, said second vortex chamber having a fluid inlet substantially near a first end of said second vortex chamber and a fluid outlet substantially near a second end of said second vortex chamber, said fluid inlet and said fluid outlet placed so that water flowing through said second vortex chamber creates a vortex with a left spin;
  a third vortex chamber being substantially tubular in shape and in communication with said water source, said third vortex chamber having a fluid inlet substantially near a first end of said third vortex chamber and a fluid outlet substantially near a second end of said third vortex chamber, said fluid inlet and said fluid outlet placed so that water flowing through said third vortex chamber creates a vortex with a right spin;

a fourth vortex chamber being substantially tubular in shape and in communication with said water source, said fourth vortex chamber having a fluid inlet substantially near a first end of said fourth vortex chamber and a fluid outlet substantially near a second end of said fourth vortex chamber, said fluid inlet and said fluid outlet placed so that water flowing through said fourth vortex chamber creates a vortex with a right spin;

a frequency antenna attached inside said fourth vortex chamber in contact with said water;

a frequency lead connecting said frequency antenna to a frequency generator, said frequency generator supplying electricity to said frequency antenna, and said frequency antenna not electrically grounded such that an electrical circuit between said frequency generator and said frequency antenna is not complete;

a metallic coil made from copper contacting said water in said third vortex chamber; and a metallic coil made from silver contacting said water in said fourth vortex chamber.

* * * * *